(12) United States Patent
Rohr et al.

(10) Patent No.: US 11,692,003 B2
(45) Date of Patent: Jul. 4, 2023

(54) MITHRAMYCIN DERIVATIVES HAVING INCREASED SELECTIVITY AND ANTI-CANCER ACTIVITY

(71) Applicant: University of Kentucky Research Foundation, Lexington, KY (US)

(72) Inventors: Jurgen Rohr, Lexington, KY (US); Oleg Tsodikov, Lexington, KY (US); Markos Leggas, Lexington, KY (US); Caixia Hou, Lexington, KY (US); Joseph Eckenrode, Lexington, TN (US); Prithiba Mitra, Lexington, KY (US); Abhisek Mandal, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 103 days.

(21) Appl. No.: 17/278,070

(22) PCT Filed: Sep. 20, 2019

(86) PCT No.: PCT/US2019/052118
§ 371 (c)(1),
(2) Date: Mar. 19, 2021

(87) PCT Pub. No.: WO2020/106357
PCT Pub. Date: May 28, 2020

(65) Prior Publication Data
US 2022/0033429 A1    Feb. 3, 2022

Related U.S. Application Data

(60) Provisional application No. 62/734,464, filed on Sep. 21, 2018.

(51) Int. Cl.
*C07H 15/24*    (2006.01)

(52) U.S. Cl.
CPC .................................. *C07H 15/24* (2013.01)

(58) Field of Classification Search
None
See application file for complete search history.

(56) References Cited

U.S. PATENT DOCUMENTS

| | | | |
|---|---|---|---|
| 8,592,379 B2 | 11/2013 | Fujii et al. | |
| 9,447,135 B2 * | 9/2016 | Rohr | C07H 15/24 |
| 11,224,609 B2 * | 1/2022 | Rohr | A61P 35/02 |

OTHER PUBLICATIONS

Mitra et al. 'Development of Mithramycin Analogues with Increased Selectivity toward ETS Transcription Factor Expressing Cancers', Journal of Medicinal Chemistry, Aug. 16, 2018 (Aug. 16, 2018), vol. 61, pp. 8001-8016.

Weidenbach et al. 'Dimerization and DNA recognition rules of mithramycin and its analogues', J Inorg Biochem. 2016, vol. 156, pp. 40-47.

* cited by examiner

*Primary Examiner* — Traviss C McIntosh, III

(74) *Attorney, Agent, or Firm* — Stites & Harbison PLLC; Mandy Wilson Decker

(57) ABSTRACT

Mithramycin (MTM) short side chain ketone (SK) derivatives and MTM short side chain diketone (SDK) derivatives are provided. The MTM SK and MTM SDK derivatives are useful for treatment of cancer or neuro-diseases associated with an aberrant erythroblast transformation-specific transcription factor. Unique MTM SK and MTM SDK derivatives have increased selectively toward ETS transcription factor.

18 Claims, 6 Drawing Sheets

Specification includes a Sequence Listing.

MITHRAMYCIN DERIVATIVES HAVING INCREASED SELECTIVITY AND ANTI-CANCER ACTIVITY

RELATED APPLICATIONS

This application is a national stage application, filed under 35 U.S.C. § 371, of International Patent Application No. PCT/US2019/052118, filed Sep. 20, 2019, which claims priority from U.S. Provisional Application Ser. No. 62/734,464, filed Sep. 21, 2018, the entire disclosures of which are incorporated herein by this reference.

GOVERNMENT INTEREST

This invention was made with government support under grant numbers CA 243529 awarded by the National Institutes of Health, and grant numbers W81XWH1610477, W81XWH1610478, W81XWH1610479 awarded by the Department of Defense, Department of Army. The government has certain rights in the invention.

TECHNICAL FIELD

The present disclosure relates to mithramycin (MTM) short side chain ketone (SK) derivatives and MTM short side chain diketone (SDK) derivatives and their use in the treatment of cancers. The unique MTM SK and MTM SDK derivative compounds disclosed herein have increased selectively toward ETS transcription factor.

BACKGROUND

All members of the erythroblast transformation-specific (ETS) transcription factor-family contain an Ets-domain, which consists of approximately 80 amino acids with four tryptophan repeats. The Ets-domain binds to double-stranded DNA of target genes containing a GGAA/T core motif and different flanking regions. Exemplary ETS transcription factors include Friend leukemia integration 1 transcription factor (FLI1) and v-ets avian erythroblastosis virus E26 oncogene-like transcription factor (ERG).

FLI1 aberrant regulation is often associated with malignant transformation and is associated with chromosomal abnormalities in humans. For example, in Ewing Sarcoma and primitive neuroectodermal tumors, a chromosomal translocation results in a chimeric EWS-FLI1 fusion protein, containing the 5' region of EWS (Ewing sarcoma breakpoint region 1) and the 3' ETS region of Fli-1 (Delattre et al., Nature. 1992 Sep. 10; 359(6391):162-5). This oncoprotein acts as an aberrant transcriptional activator with strong transforming capabilities. FLI1 and homologous transcription factors also have been implicated in human leukemias, such as Acute Myelogenous Leukemia (AML), involving loss or fusion of the tel gene, as well as other malignancies including clear-cell sarcoma, myxoid liposarcoma, desmoplastic small round cell tumor, myxoid chondrosarcoma, acute myeloid leukemia, congenital fibrosarcoma, prostate cancer and pancreatic cancer.

Another ETS transcription factor, ERG, is implicated in several cancers. Aberrant ERG regulation has been shown to be associated with diseases including Ewing sarcoma, acute myeloid leukemia (AML), prostate cancer, acute lymphoblatic leukemia (ALL), Alzheimer's disease (AD), and Down syndrome (DS).

Although ETS transcription factors such as FLI1 and ERG have been identified as critical targets in diseases such as Ewing sarcoma, no therapies have yet moved from bench to bedside that could impact the outcome of this disease. Ewing sarcoma, which affects primarily children and young adults is a difficult cancer to treat. Current therapy with a combination of severely cytotoxic drugs provides up to 60% long-term survival, but the cancer often recurs.

Mithramycin (MTM), an aureolic acid natural product previously used clinically against other cancers, was identified as a potent (low-nM) inhibitor of EWS-FLI1 in Ewing sarcoma cells (Grohar et al., (2011) Journal of the National Cancer Institute 103, 962-78). MTM exhibited similar high potency against Ewing sarcoma tumor cells in vitro and was efficacious in Ewing sarcoma mouse xenografts. Based on this study, MTM entered clinical trials at the National Cancer Institute as a Ewing sarcoma therapeutic (ClinicalTrials.gov, ID #NCT01610570) in 2012. Despite its strong inhibitory properties towards Ewing sarcoma, MTM was found to be highly toxic to non-Ewing cells, apparently because it inhibits Sp transcription factors. Therefore, MTM analogues that are more selective against Ewing sarcoma cells and/or other cancers are needed. MTM has high potential in the fight against cancer and new and improved analogues would find clinical relevance. A need thus exists to improve the performance, selectivity and efficacy of MTM.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Mithramycin (MTM; 1, FIG. 1) is an aureolic acid-type polyketide drug produced by various soil bacteria of the genus *Streptomyces* and was found to possess activity against a wide variety of human cancers.[1-2] MTM (1) was clinically evaluated in the 1960s and 70s as an agent for the chemotherapy of various cancers. As noted above, despite some remarkable success using MTM (1) as a single agent, the results were mixed due to its narrow therapeutic index and considerable variation in patients' ability to tolerate the drug.[3] Another concern was the lack of understanding of MTM's (1) mode-of-action. Taken together these limitations limited clinical use of MTM (1) as a chemotherapeutic agent and it has now been largely abandoned.[4] Interest in MTM (1) was renewed recently, after the drug was identified as the top inhibitor of the ETS transcription factor fusion, EWS-FLI1, in a screen of more than 50,000 natural products and synthetic compounds. FLI1 and ERG are ETS transcription factors that are expressed as fusions with EWS and are the primary cause of Ewing sarcoma.[5-6]

Aside from Ewing sarcoma, aberrant ETS transcription factors contribute significantly to the malignancy of prostate cancer, leukemia and lymphoma. With respect to prostate cancer, approximately 50% of patients express a truncated form of ERG as a result of the TMPRSS2 (transmembrane protease, serine 2)-ERG gene fusion.[7] Interestingly, the DNA binding domain of ERG and FLI1 is conserved and thus molecules that interfere with the activity of one should also inhibit the other. Given the importance of these aberrant transcription factors in driving malignancy, the clinical use of MTM (1) gave investigators hope for a "targeted" therapy. This was tested in a recent national cancer institute (NCI) conducted clinical study where Ewing sarcoma patients were enrolled to assess the utility of MTM (1) in a population of patients, all of whom express ETS fusions. Unfortunately, the results were inconclusive because the trial was terminated early, due to toxicities. As such, the development of less toxic and more selective analogues of MTM (1) is highly desirable.

As disclosed herein, the present inventors have identified a number of derivatives, including those identified based on mechanistic studies that focused on understanding MTM's (1) mechanism of action. At the molecular level, it is known that MTM (1) binds to GC-rich DNA as a $Mg^{2+}$ coordinated dimer and modulates the activity of the transcription factor Sp1 (specificity protein 1) and presumably others.[8]

Mithramycin SK (MTMSA; 2, FIG. 1) and mithramycin SDK (MTM SDK: 3, FIG. 1) are combinatorial biosynthetic analogues of MTM (1) produced by *S. argillaceus*, upon inactivation of the mtmW gene.[9] The MTM SK and MTM SDK derivatives disclosed herein include amino acid derivatives and dipeptide derivatives. The MTM SK and MTM SDK derivatives are useful for treatment of cancer or neuro-diseases associated with an aberrant erythroblast transformation-specific transcription factor, as disclosed herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

BRIEF DESCRIPTION OF THE SEQUENCE LISTING

SEQ ID NO: 1 is an amino acid sequence for a DNA-binding domain (DBD) of target ETS transcription factor.

SEQ ID NO: 2 is another amino acid sequence for a DNA-binding domain (DBD) of target ETS transcription factor.

SEQ ID NO: 3 is an amino acid sequence of FLI1 transcription factor.

SEQ ID NO: 4 is an amino acid sequence of ERG transcription factor.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes MTM-SK and MTM-SDK derivatives useful for treatment of cancer and other conditions, including diseases associated with an aberrant erythroblast transformation-specific transcription factor.

Figure 1:
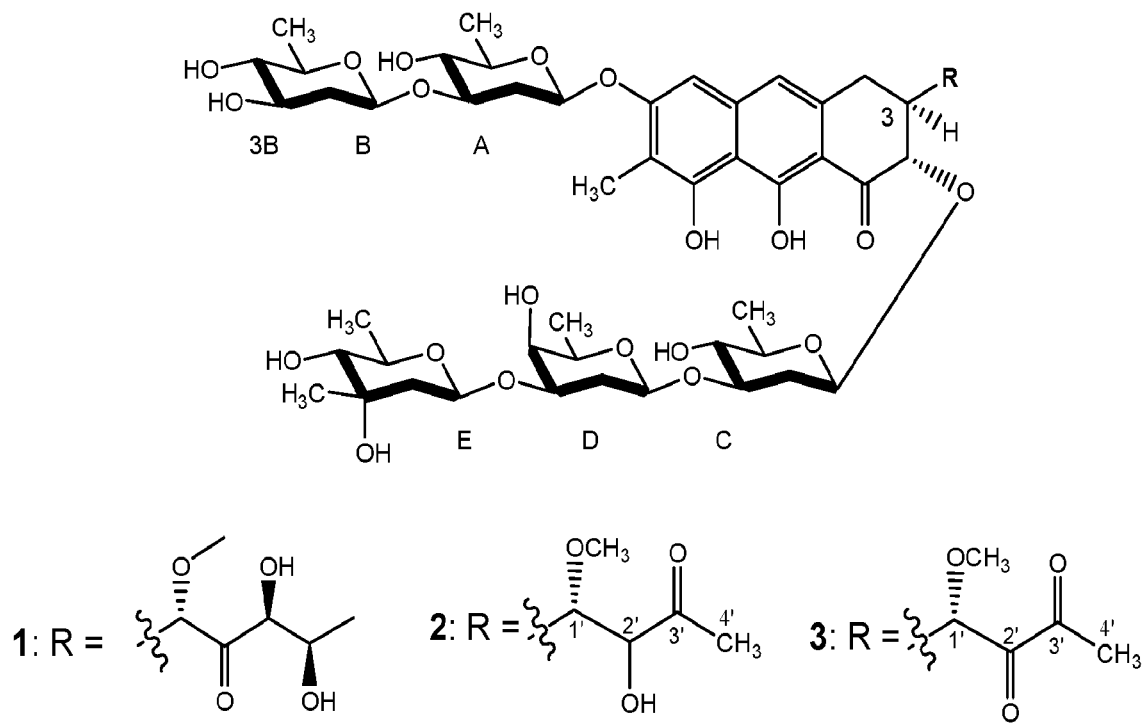
FIG. 1 includes the structure of Mithramycin (MTM; 1), Mithramycin SK (MTM SK; 2), and Mithramycin SDK (MTM SDK-Trp; 3).
Figure 2:
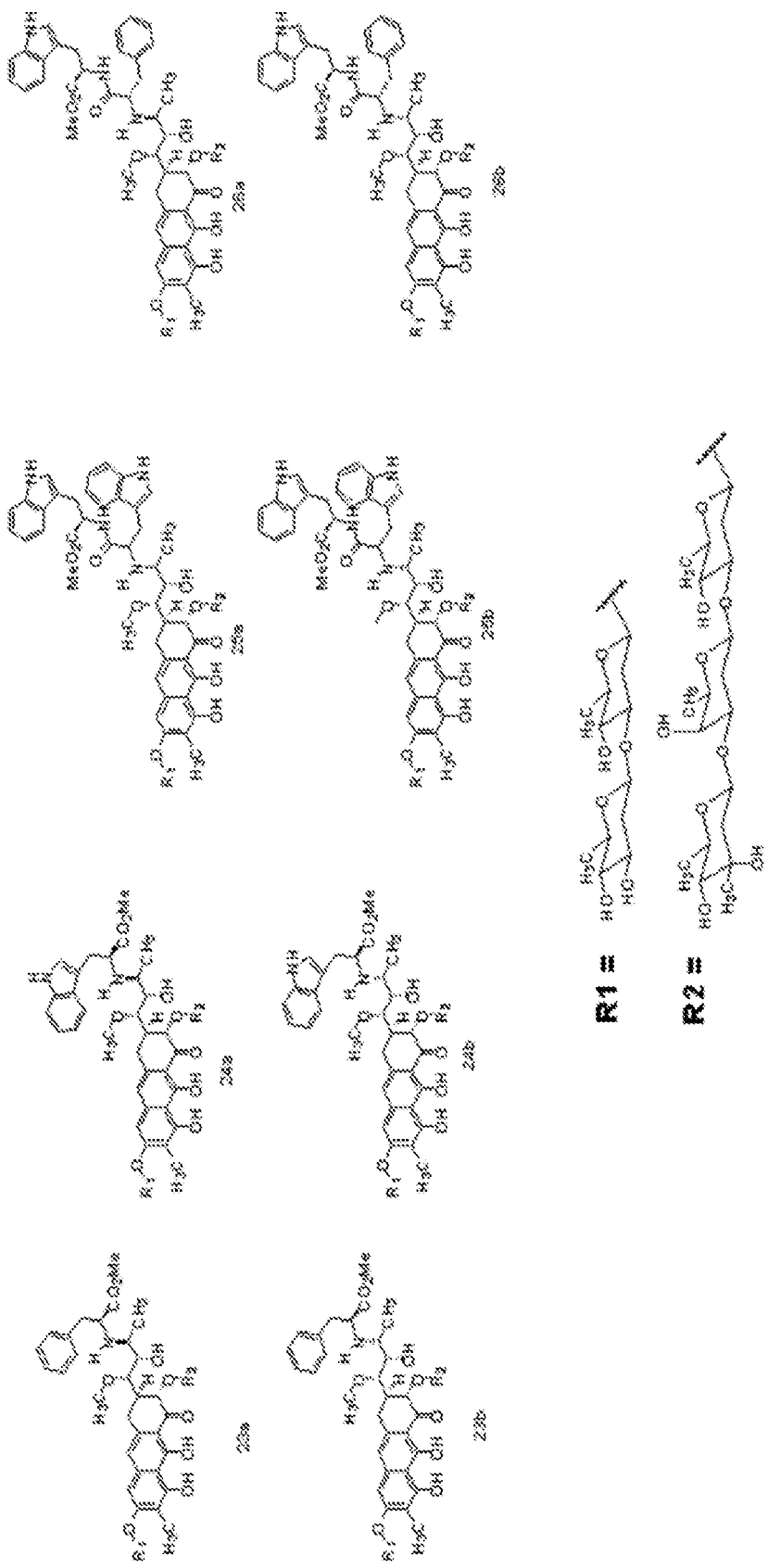
FIG. 2 includes a series of exemplary MTM SK amine analogues in accordance with the presently-disclosed subject matter.
Figure 3:
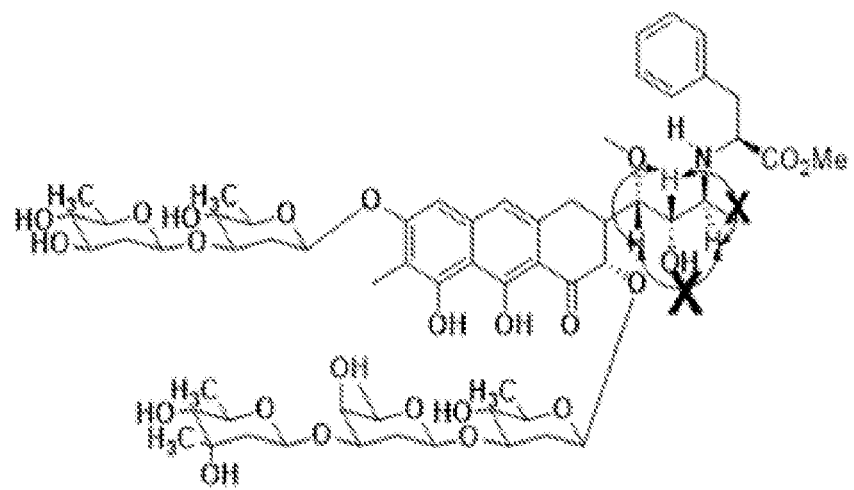
FIG. 3 illustrates a NOESY Experiment of MTM-SK-Phenylalanine (Phe), which was used to determine the stereochemistry of the compound.
Figure 4:
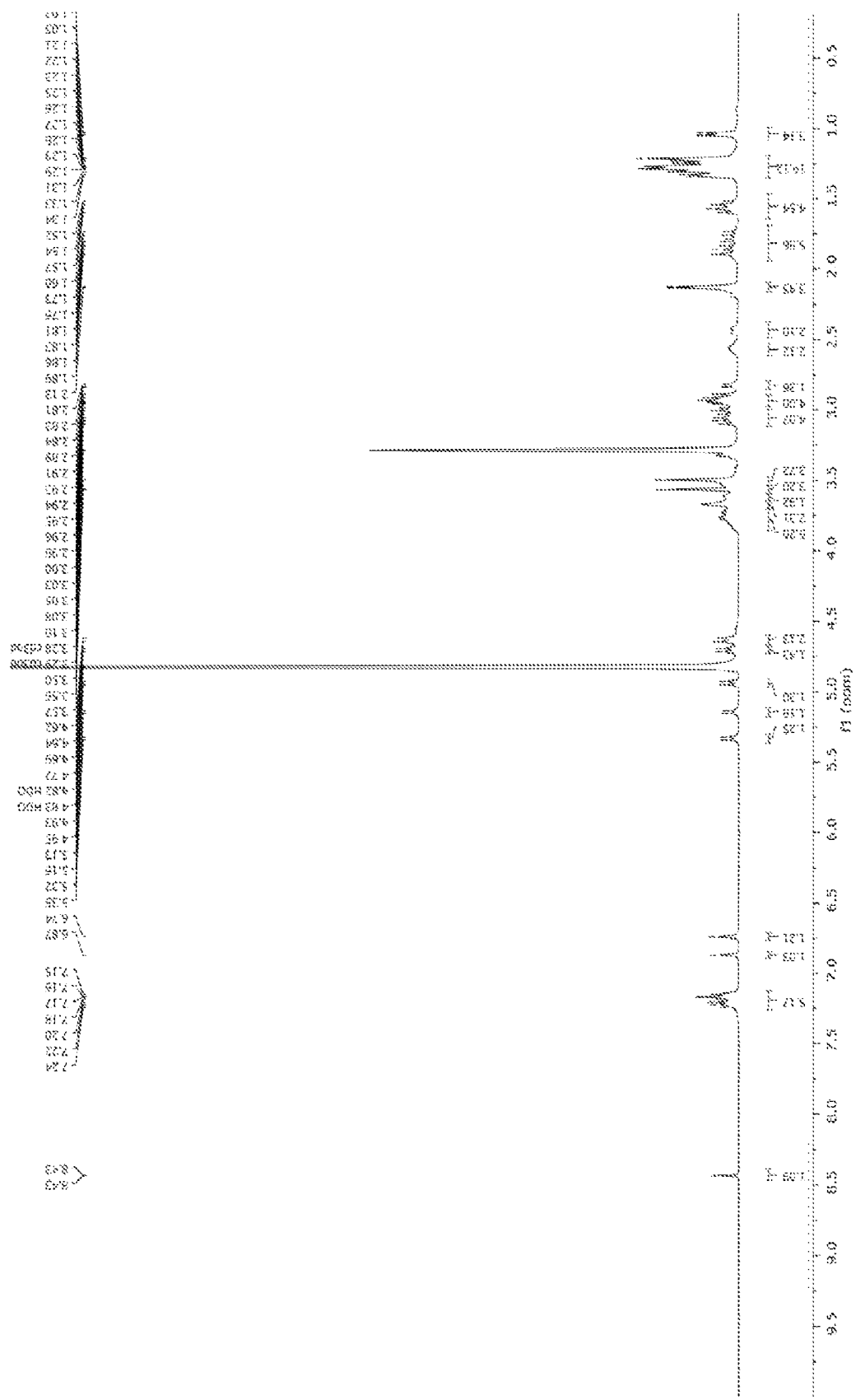
FIG. 4 includes an $^1$H NMR (400 MHz, $CD_3OD$) spectrum of MTM-SK-Phe.
Figure 5:
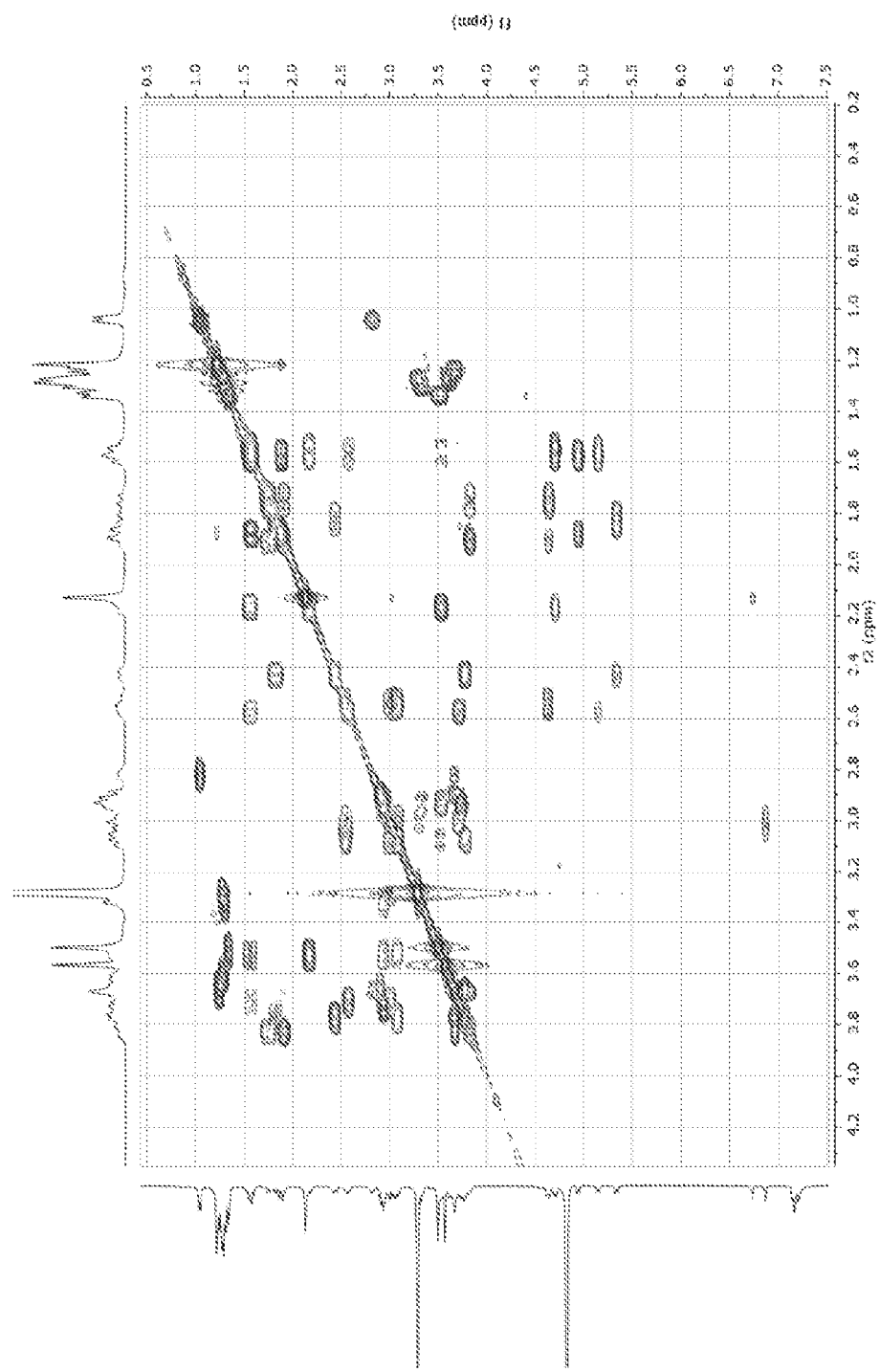
FIG. 5 includes a COSY Spectra (1H-1H Correlation) of MTM-SK-Phe.
Figure 6:
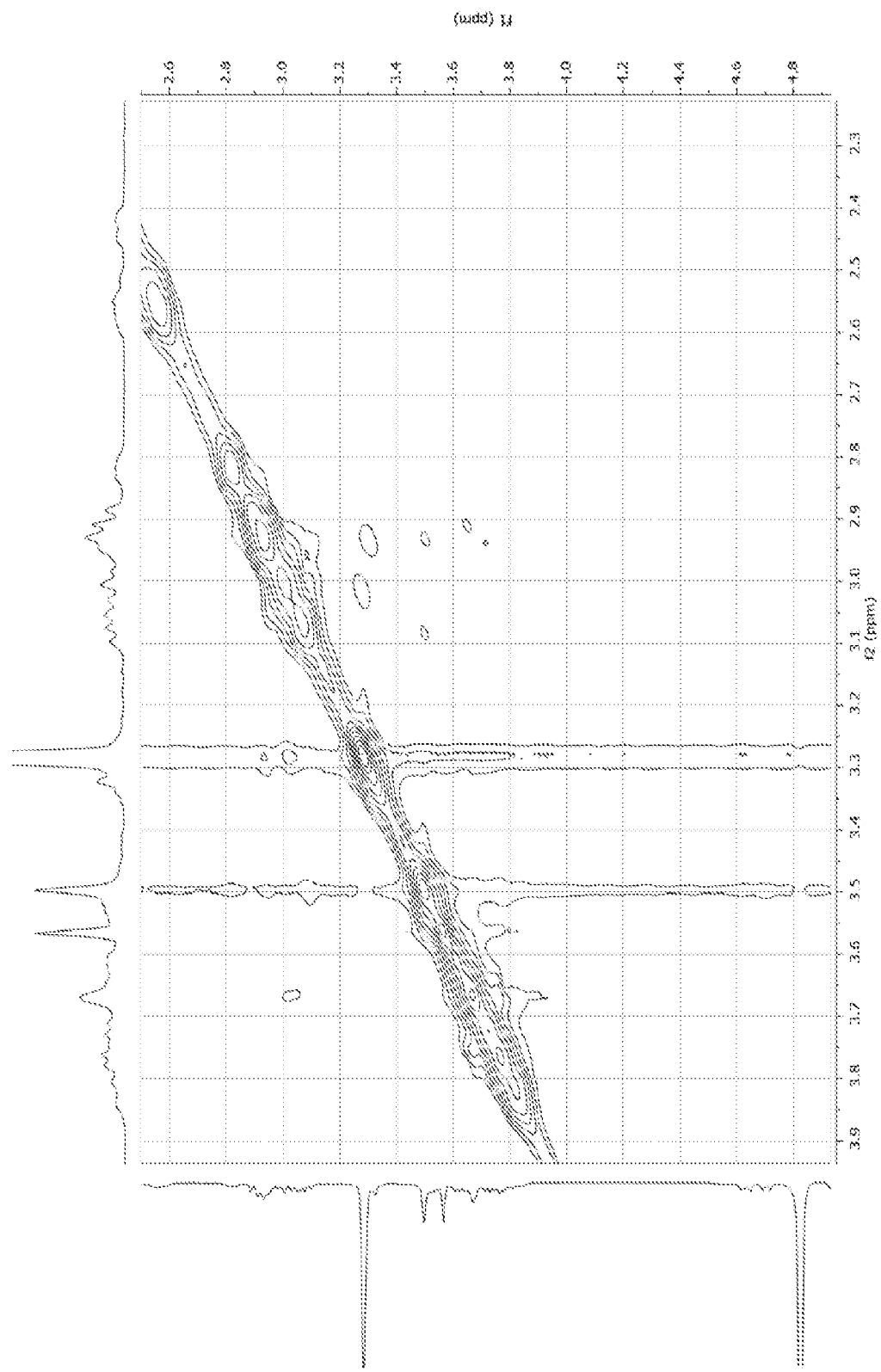
FIG. 6 includes a NOESY Spectra (1H-1H Correlation) of MTM-SK-Phe.

The MTM-SK and MTM-SDK derivatives of the subject technology can be synthesized according to the methods described below in view of the knowledge of the skilled artisan. The inactivation of the mtmW gene, which is the gene encoding the last acting enzyme in the MTM biosynthetic pathway, produced MTM analogues with a short side chain ketone (SK) and MTM with a short side chain diketone (SDK) (FIG. 1). Both of these analogues possess shorter side chains at the 3-position. The 3-side chain has been identified previously as important, since it is in part responsible for MTM's interaction with the DNA phosphate backbone. See U.S. Pat. No. 7,423,008. Both MTM SK and MTM SDK showed increased activity against several cancer cell lines compared to the parent MTM. These results indicate that the 3-side chain is important for the activity of MTM and offers a base for further molecular manipulations.

MTA SK is shown in formula (IA) below, and MTM SDK is shown in formula (IB) below:
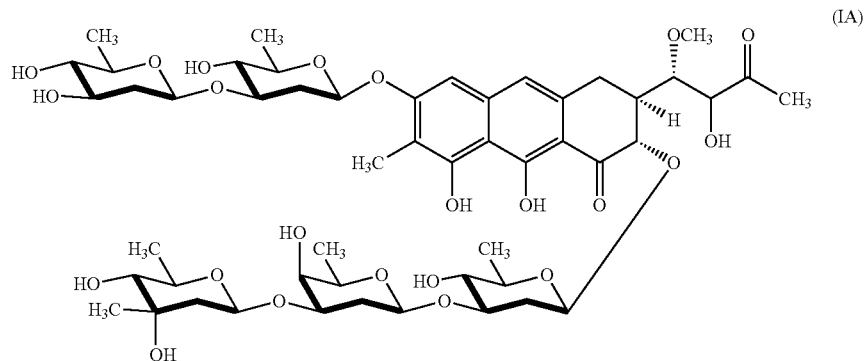
(IA)
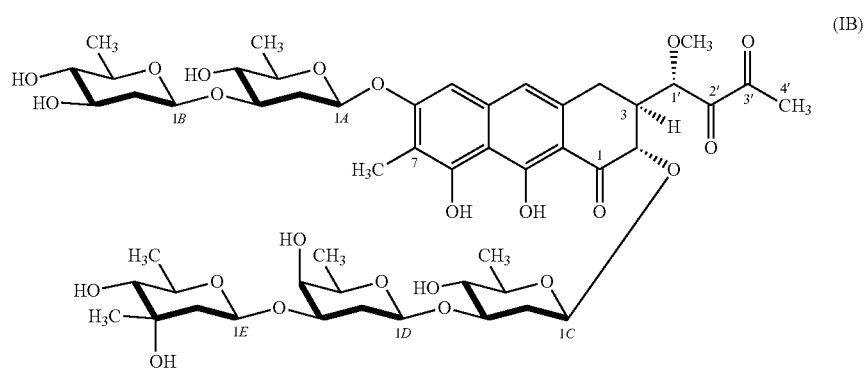
(IB)
The compounds can also be represented by formula (IC), in which R¹ is either —OH or =O:
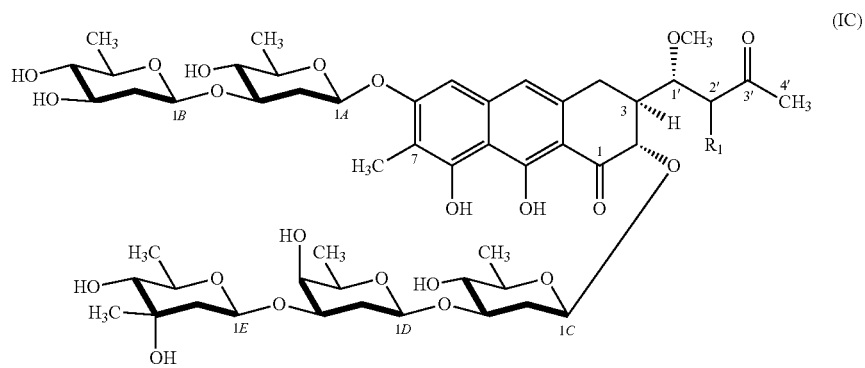
(IC)

Derivatives disclosed herein are made by coupling a synthetic moiety composed of aromatic substructures, such as the amino acid derivatives or dipeptide derivatives MTM SK or MTM-SDK.

In one aspect of the present disclosure, the MTM-SK and MTM-SDK derivatives have the following formula (II), in which $R^2$ is a synthetic moiety:

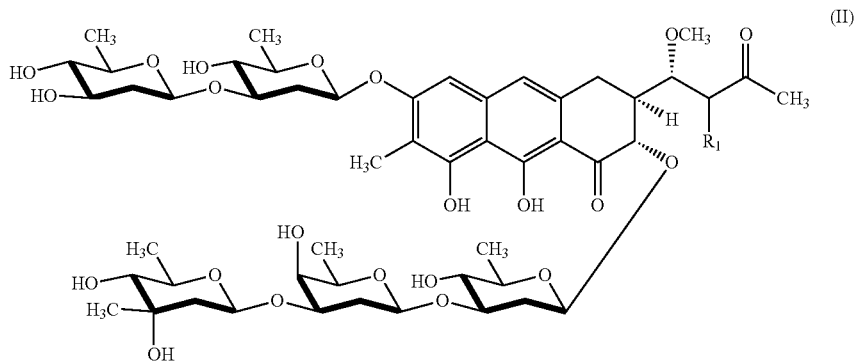

Formula (II) is also represented herein as: "MTM-SK/SDK-$R^2$."

The A, B, C, D, E, sugars can be different from those shown, and include chain variants. Such sugars are disclosed, for example, in: (a) Baig, I.; Pérez, M.; Braña, A. F.; Gomathinayagam, R.; Damodaran, C.; Salas, J. A.; Méndez, C.; Rohr, J., Mithramycin analogues generated by combinatorial biosynthesis show improved bioactivity. *J. Nat. Prod.* 2008, 71 (2), 199-207; (b) Pérez, M.; Baig, I.; Braña, A. F.; Salas, J. A.; Rohr, J.; Méndez, C., Generation of new derivatives of the antitumor antibiotic mithramycin by altering the glycosylation pattern through combinatorial biosynthesis. *ChemBioChem* 2008, 9 (14), 2295-2304; (c) Nuñez, L. E.; Nybo, S. E.; Gonzalez-Sabin, J.; Pérez, M.; Ménendez, N.; Braña, A. F.; He, M.; Morís, F.; Salas, J. A.; Rohr, J.; Méndez, C., A Novel Mithramycin Analogue with High Antitumor Activity and Less Toxicity Generated by Combinatorial Biosynthesis. *J. Med. Chem.* 2012, 55, 5813-5825; (d) Remsing, L. L.; Garcia-Bernardo, J.; Gonzalez, A. M.; Künzel, E.; Rix, U.; Braña, A. F.; Bearden, D. W.; Méndez, C.; Salas, J. A.; Rohr, J., Ketopremithramycins and ketomithramycins, four new aureolic acid-type compounds obtained upon inactivation of two genes involved in the biosynthesis of the deoxysugar moieties of the antitumor drug mithramycin by *Streptomyces argillaceus*, reveal novel insights into post-PKS tailoring steps of the mithramycin biosynthetic pathway. *J. Am. Chem. Soc.* 2002, 124 (8), 1606-1614; (e) Remsing, L. L.; Bahadori, H. R.; Carbone, G. M.; McGuffie, E. M.; Catapano, C. V.; Rohr, J., Inhibition of c-src transcription by mithramycin: structure-activity relationships of biosynthetically produced mithramycin analogues using the c-src promoter as target. *Biochemistry* 2003, 42 (27), 8313-8324. Pharmaceutically acceptable salts of the MTM SK and MTM SDK derivative are also contemplated by the present disclosure.

In some embodiments, the MTM-SK or MTM SDK derivative can be a substituted tryptophan (Trp) derivative. In some embodiments, the MTM SK or MTM SDK derivative can have the following formula (III), in which $R^1$ is either —OH or =O, and which can also be represented by formula (IV):

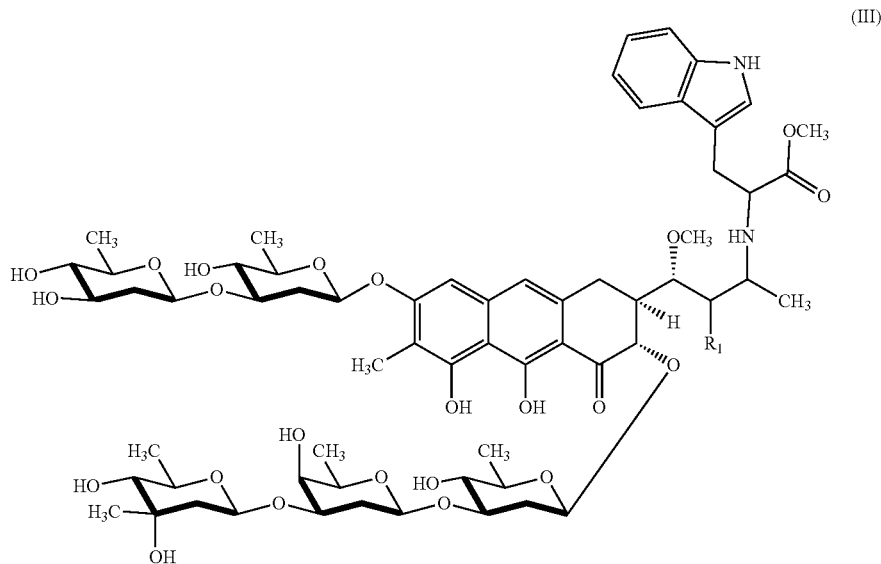

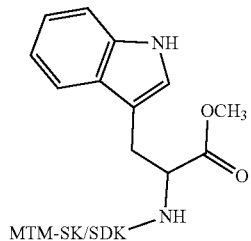
(IV)
In some embodiments, the MTM SK or MTM SDK derivative can be a substituted phenylalanine (Phe) derivative. In some embodiments, the MTM SK or MTM SDK derivative can have the following formula (V), which can also be represented by formula (VI):
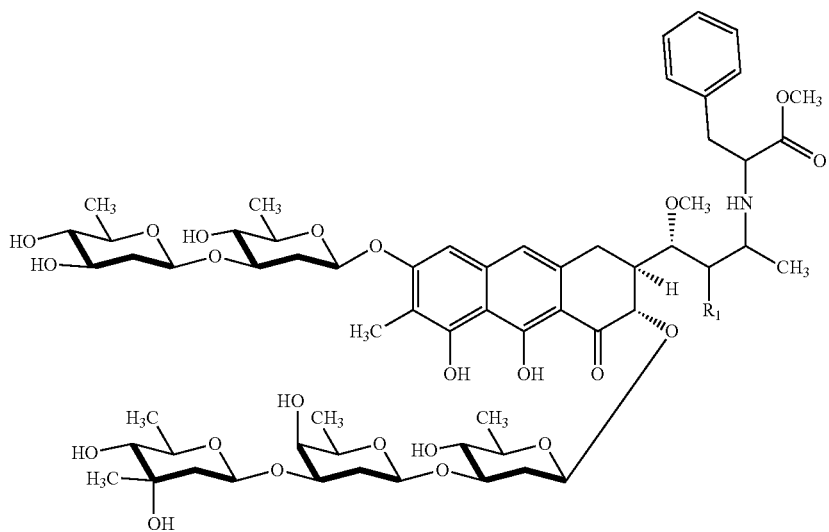
(V)
(VI)

In some embodiments, the MTM SK or MTM SDK derivative can be a substituted with dipeptides, such as amino acid dipeptides. In some embodiments, the MTM SK or MTM SDK derivative can be substituted with Phe-Phe, Trp-Trp, Phe-Trp, or Trp-Phe.

In some embodiments, the MTM SK or MTM SDK derivative has the structure of one of formulae (V)-(VIII):

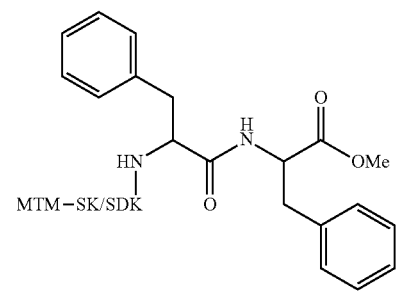

(V)

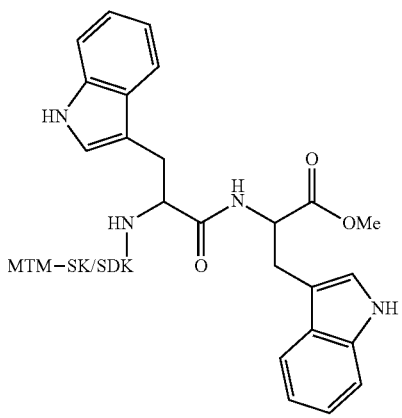

(VI)

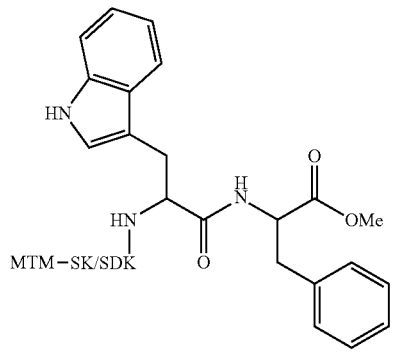

(VII)

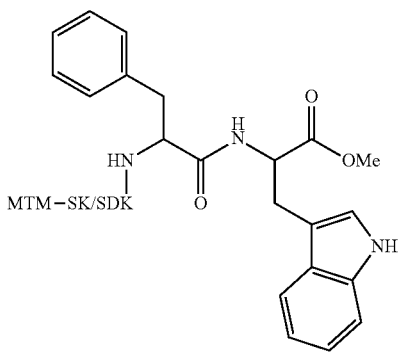

(VIII)

The MTM SK and MTM SDK derivatives of the present disclosure can be used for the treatment of cancer, such as brain, colon, prostate, lung, breast, esophageal, pancreatic, skin, Ewing sarcoma, any type of blood cancer etc. MTM derivatives are also neuroprotective and the MTM SK and MTM SDK derivatives can be used to treat various neuro-diseases, such as Huntington disease, etc.

The biosynthesis of MTM SK and MTM SDK is accomplished through a genetically engineered *S. argillaceus* strain, M7W1, which contains an inactivated mtmW gene coding for the MtmW enzyme. Both the MTM SK and MTM SDK analogues have improved activity compared to the parent MTM compound. The activity of the MTM SK and MTM SDK derivatives disclosed herein is further improved.

Methods of Treatment

In one aspect, the subject technology provides a method for selectively modulating the activity of a target ETS transcription factor in a patient in need thereof, including administering to the patient a therapeutically effective amount of an MTM SK or MTM SDK derivative or a pharmaceutically acceptable salt thereof, as described herein.

In an embodiment relating to this aspect, the subject technology provides a method for selectively modulating the activity of a target ETS transcription factor in a patient with Ewing sarcoma or prostate cancer for example. The method includes administering to the patient a therapeutically effective amount of the MTM SK or MTM SDK derivative. In some embodiments relating to this aspect, the ETS transcription factor includes a DNA binding domain with an amino acid sequence that is at least 85% identical to SEQ ID NO: 1 or SEQ ID NO: 2 over the entire length of either of these sequences.

In another aspect, the subject technology provides a method of treating a target ETS transcription factor-mediated disease in a patient by administering to the patient a therapeutically effective amount of an MTM SK or MTM SDK derivative described herein, wherein the MTM SK or MTM SDK derivative specifically modulates the activity of the ETS transcription factor mediating the disease and wherein the target ETS-mediated disease is Ewing sarcoma, clear-cell sarcoma, myxoid liposarcoma, desmoplastic small round cell tumor, myxoid chondrosarcoma, acute myeloid leukemia, congenital fibrosarcoma, prostate cancer or pancreatic cancer, for example. The following Table lists several ETS transcription factors that may be modulated and associated diseases that may be treated with the subject technology.

| ETS Transcription factors and associated diseases. | |
|---|---|
| Transcription factor | Disease |
| ETS-1 | Meningioma, invasive carcinoma of the breast, colorectal carcinoma, pancreatic carcinoma, adenocarcinoma, thyroid carcinoma; thymoma, angioma |
| ETS-2 | Breast cancer |
| ERG | TMPRSS2: ERG fusion in prostate cancer EWS-ERG fusion in Ewing Sarcoma ERG overexpression in AML |
| FLI1 | EWS-FLI1 fusion in Ewing Sarcoma |
| PEA3 | Invasive breast carcinoma |
| ER81 | EWS-ER81 fusion in Ewing sarcoma, prostate carcinoma, breast carcinoma |
| ELF-1 | Prostate, ovarian and breast cancers, leukemia, and lymphoma. |

ETS Transcription factors and associated diseases.

| Transcription factor | Disease |
| --- | --- |
| TEL/ETV6 | TEL fusion protein partners (PDGFbetaR, TRKc, ABL, and JAK2) in leukemia and fibrosarcoma |
| PU.1/SPI1 | Promyelocytic leukemia, acute myelocytic leukemia |
| Myc | Burkitt lymphoma, B-cell lymphoma, multiple myeloma, medulloblastoma, neuroblastoma, colorectal, ovarian, and intestinal cancer |

In general, the MTM SK and MTM SDK derivatives of the present disclosure can be used for the treatment of a target ETS transcription factor-mediated disease including Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblatic leukemia (ALL), Alzheimer's disease (AD), or Down syndrome (DS) or other hyperproliferative disease in which an aberrant activity of a target ETS transcription factor is implicated. A "hyperproliferative disease" includes diseases and conditions that are associated with any sort of abnormal cell growth or abnormal growth regulation, specifically a cancer.

Some MTM derivatives are more specific than MTM for complexing with a target EST transcription factor and, therefore, inhibiting its activity. The specific or selective MTM SK and MTM SDK derivatives of the subject technology are useful for treating diseases that are mediated by, for example, FLI1 or ERG, such as Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblatic leukemia (ALL), Alzheimer's disease (AD), or Down syndrome (DS) or other hyperproliferative disease in which an aberrant activity of a target ETS transcription factor is implicated.

Other hyperproliferative diseases which may be benefited by the methods and compounds of the subject technology include, though it is not limited to, neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In another aspect of the present disclosure, an effective amount of the MTM SK or MTM SDK derivative or a pharmaceutically acceptable salt thereof is administered to a patient in need of cancer treatment or a neuro-disease, such as Huntington's disease. The MTM SK or MTM SDK derivatives or pharmaceutically acceptable salts thereof of the present disclosure can be administered to a patient, e.g., a human patient, in need of such treatment by any route. The MTM SK or MTM SDK derivatives or pharmaceutically acceptable salts thereof of the present disclosure can be administered alone or with a pharmaceutically acceptable carrier or excipient.

Dosage Form and Formulation of MTM SK and MTM SDK Derivatives

An MTM SK or MTM SDK derivative as described herein can be administered to a patient in need thereof in any possible dosage form including, but not limited to ingestible tablets, buccal tablets, troches, capsules, elixirs, suspensions, syrups, wafers, infusion, aqueous liquid and the like. Solutions of an MTM SK or MTM SDK can be prepared in water and mixed with suitable excipients. Under ordinary conditions of storage and use, these preparations can contain a preservative to prevent the growth of microorganisms or retain stabilization of the MTM SK or MTM SDK derivative. The pharmaceutical forms suitable for injection include sterile aqueous solutions or dispersions and sterile powders for the extemporaneous preparation of sterile injectable solutions or dispersions. The form should be sterile and should be fluid to the extent it makes injection possible.

A composition containing an MTM SK or MTM SDK derivative can be prepared by known methods, such that an effective quantity of the therapeutic agent is delivered to a subject. Suitable vehicles for such a composition are described, for example, in Remington's Pharmaceutical Sciences (2003) and in the Handbook of Pharmaceutical Additives (compiled by Michael and Irene Ash, Gower Publishing Limited, Aldershot, England (1995)).

In some embodiments, the composition of this disclosure enables sustained, continuous delivery of an MTM SK or MTM SDK derivative to tissues adjacent to or distant from an administration site. The biologically-active agent is capable of providing a local or systemic biological, physiological or therapeutic effect. For example, the MTM SK or MTM SDK derivative may act to kill cancer cells or cancer stem cells or to control or suppress tumor growth or metastasis, among other functions.

In some embodiments, the formulations of the present disclosure are administered in an amount effective to provide the desired level of biological, physiological, pharmacological and/or therapeutic effect such as inhibition of a target ETS transcription factor.

The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical formulations include, for example, at least about 0.1% of an active compound, such as MTM SK or MTM SDK or derivatives thereof or pharmaceutically acceptable salt thereof. In other embodiments, the active compound may comprise between about 1% to about 75% of the weight of the unit dosage, or between about 5% to about 50% by weight of the unit dosage, for example, and any specific percentage in between these ranges. In other non-limiting examples, a dose may also comprise from about 0.01 microgram/kg/body weight, about 50 microgram/kg/body weight, about 100 microgram/kg/body weight, about 500 microgram/kg/body weight, about 1 milligram/kg/body weight, about 5 milligram/kg/body weight, about 10 milligram/kg/body weight, about 30 milligram/kg/body weight, about 40 milligram/kg/body weight, about 50 milligram/kg/body weight, about 100 milligram/kg/body weight, or more per administration, and any range or specific amount derivable therein. In non-limiting examples of a derivable range from the numbers listed herein, a range of about 5 microgram/kg/body weight to about 5 milligram/kg/body weight, about 50 microgram/kg/body weight to about 50 milligram/kg/body weight, etc., can be administered.

For a safe and effective dosage, the formulations can be administered at an MTM SK or MTM SDK derivative dose of about 0.01 to about 500 mg/m$^2$ (body surface)/day, about 0.01 to about 300 mg/m$^2$/day, 0.01 to about 200 mg/m$^2$/day, about 1 to about 200 mg/m$^2$/day about 10 to about 100 mg/m$^2$/day, about 25 to about 100 mg/m$^2$/day or any range derivable therein to a subject such as a human. In certain aspects, the composition may be administered at a dose of about 0.01 to about 200 mg/kg body weight, about 0.01 to about 100 mg/kg body weight, 1 to about 50 mg/kg body weight, about 1 to about 20 mg/kg body weight, about 3 to about 10 mg/kg body weight, about 3 to about 6 mg/kg body weight or any range derivable therein to a subject such as a human. In some embodiments, a formulation of the subject technology may be administered in a dose of 1, 2, 3, 4, 5, 6, 7, 8, 9, 10, 15, 20, 25, 30, 40, 50, 60, 70, 80, 90, 100 mg or more per day. Each liquid dose may be in a volume of 1, 10, 50, 100, 200, 500, 1000 or more µl or ml.

In some embodiments, the pharmaceutical formulation of the subject technology includes an MTM SK or MTM SDK derivative in an amount effective to result in a serum concentration of the MTM SK or MTM SDK in the mammal in a range of from 1 nM to 1 mM, particularly 1 nM to 2 µM.

Serum and systemic circulation concentrations of MTM SK or MTM SDK derivatives effective to result in the treatment of a target ETS transcription factor-mediated disease may vary depending on a number of factors. Influential variables can include, for example, pKa, solubility or molecular weight of the MTM SK or MTM SDK derivative. These properties of a particular MTM SK or MTM SDK derivative may affect how a patient metabolizes the compound, how much of the compound enters and remains in the systemic circulation of the patient, and how effectively the compound treats, prevents or causes regression of the disease, e.g., Ewing sarcoma, tumor or cancer.

Precise amounts of the therapeutic composition also depend on the judgment of the practitioner and are peculiar to each individual. Factors affecting the dose include the physical and clinical state of the patient, the route of administration, the intended goal of treatment (e.g. alleviation of symptoms versus cure) and the potency, stability and toxicity of the particular therapeutic substance.

Route of Administration

In accordance with the methods of the disclosure, the described composition or formulation of the subject technology may be administered to a subject in a variety of forms depending on the selected route of administration, as will be understood by those skilled in the art. It may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, intratumoral, transepithelial, nasal, intrapulmonary, intrathecal, rectal and topical modes of administration. Parenteral administration may be by continuous infusion over a selected period of time.

Combination Therapies

In certain embodiments, the compounds, compositions or formulations of the subject technology are administered with a second or additional active agent(s) such as with one or more different MTM SK or MTM SDK derivatives or another anticancer agent. Such therapy can be applied in the treatment of any disease for which treatment with an MTM SK or MTM SDK derivative is contemplated. For example, the disease may be a hyperproliferative disease, such as Ewing sarcoma or prostate cancer.

In certain embodiments, the additional active agent may be a chemotherapeutic agent or a radiation therapy. Examples of chemotherapeutic agents include, but are not limited to, cetuximab (erbitux), herceptin (trastuzumab), fludarabine, cyclophosphamide, rituximab, imatinib, Dasatinib (BMS0354825), cisplatin (CDDP), carboplatin, procarbazine, mechlorethamine, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabien, navelbine, farnesyl-protein tansferase inhibitors, transplatinum, 5-fluorouracil, vincristin, vinblastin, methotrexate, an analogue or derivative thereof. In certain embodiments, the active or anticancer agent(s) that may be used in combination with an MTM SK or MTM SDK derivative may be fludarabine, cyclophosphamide, rituximab, imatinib or Dasatinib. In a certain aspect, the cancer may be resistant to a particular chemotherapeutic agent, such as fludarabine, cyclophosphamide, rituximab, imatinib or Dasatinib.

To facilitate an understanding of the present subject technology, a number of terms and phrases are defined below:

A reference to an element in the singular is not intended to mean "one and only one" unless specifically stated, but rather "one or more."

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —CH$_2$HC═CH$_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

As used herein, a "target ETS transcription factor" refers to a transcription factor, which comprises a DNA-binding domain (DBD) having an amino acid sequence that is at least 85% identical to SEQ ID NO: 1 or SEQ ID NO: 2 over the entire length of either of these sequences. SEQ ID NO: 1 and SEQ ID NO: 2 are set forth in an Appendix submitted herewith and incorporated herein by reference.

As used herein the term "modulator," "modulating," or "modulate" in connection with the target ETS transcription factor of the subject technology refers to any agent that has a functional effect on the transcription factor, including positively or negatively affecting its binding to a DNA substrate, positively or negatively affecting the formation and/or stability of a complex formed between the transcription factor and its oligonucleotide substrate, positively or negatively affecting its function in causing the transcription of its oligonucleotide substrate.

As used herein, the term "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "variant" in relation to the amino acid sequence of the ETS transcription factors refers to a naturally occurring allelic variant of the ETS transcription factors such as those shown in SEQ ID NO: 3 and SEQ ID NO: 4, which includes any substitution of, variation of, modification of, replacement of, deletion of or addition of one (or more) amino acids provided the resultant ETS transcription factor has a transcription factor activity and has a DNA binding domain that is at least 85% identical to SEQ ID NO: 1 or SEQ ID NO: 2 over the entire length of either of these sequences. For example, a variant of ETS transcription factor may have at least 50%, or at least 60%, or at least 70% sequence identity with the ETS transcription factors such as those shown in SEQ ID NO: 3 and SEQ ID NO: 4 over the entire length of the sequence, provided that the variant has a transcription factor activity and has a DNA binding domain that is at least 85%, at least 90%, at least 95% or at least 98% identical to SEQ ID NO: 1 or SEQ ID NO: 2 over the entire length of either of these sequences.

The terms "percentage of sequence identity" or "percentage homology" and any equivalent terms are used interchangeably herein to refer to comparisons among polynucleotides and polypeptides, and are determined by comparing two optimally aligned sequences over a comparison window, wherein the portion of the oligonucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB [Pearson and Lipman, (1988), Proc. Natl. Acad. Sci. USA 85(8): 2444-2448; Altschul et al., (1990), J. Mol. Biol. 215(3):403-410; Thompson et al. (1994), Nucleic Acids. Res. 22(2): 4673-4680; Higgins et al., (1996), Meth. Enzymol. 266:383-402; Altschul et al., (1993), Nature Genetics 3:266-272; Brutlag et al. (1990) Comp. App. Biosci. 6:237-24], the disclosures of which are incorporated by reference in their entireties. In an embodiment, protein and nucleic acid sequence identities are evaluated using the Basic Local Alignment Search Tool ("BLAST") which is well known in the art [e.g., Karlin and Altschul, (1990), Proc. Natl. Acad. Sci. USA 87:2267-2268; Altschul et al., (1997), Nuc. Acids Res. 25:3389-3402] the disclosures of which are incorporated by reference in their entireties.

As used herein, an "oligonucleotide substrate" in reference to a substrate of a target ETS transcription factor refers to an oligonucleotide which comprises a target ETS transcription factor binding site. An oligonucleotide substrate can be single-stranded, double-stranded, or a hairpin. Preferably, an oligonucleotide substrate is double stranded. An oligonucleotide substrate can be DNA, RNA or a chimeric (comprising both deoxy and ribose nucleotides) or comprise one or more oligonucleotide modifications described herein.

As used herein, the term "transcription factor binding site" refers to a nucleic acid sequence that is recognized and bound by a transcription factor and mediates the transactivation of a reporter gene in response to that binding. Without limitations, a transcription binding site can be from any of various species including human, mouse, rat, guinea pig and the like. In some embodiments, the transcription factor binding site is a target ETS binding site such as a FLI1 binding site or an ERG binding site.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

Examples

Upon inactivation of mtmW, *S. argillaceus* produced two mithramycin analogues, MTMSK and MTMSDK, in addition to MTMSA.[9] MTMSK is the major product. The 3'-keto group in the 3-side chain of MTMSK/SDK was derivatized.[28]

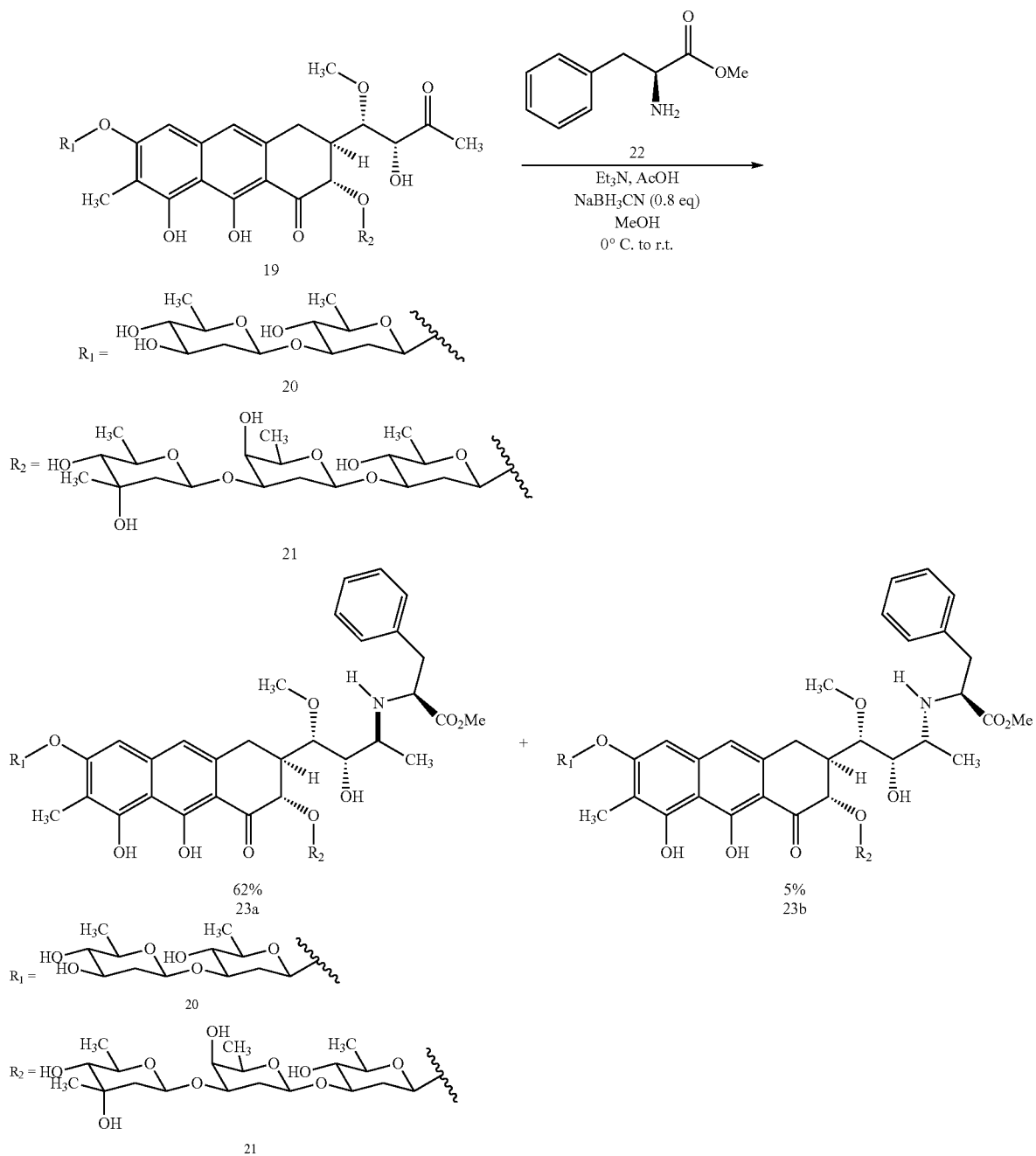

Synthesis of MTMSK Amine analogues

General Procedure for Reductive Amination:

To a methanolic solution of MTMSK 19 (1.0 equiv), amine (3.0 equiv) was added. After the addition of TEA (triethylamine, 5.0 equiv.), the reaction mixture was stirred at 0° C. for 15 min. Then acetic acid (10% of the total volume of the reaction) was added and stirred at r.t for 1 h. The reaction mixture was again cooled to 0° C. prior to the addition of NaBH$_3$CN (0.8 equiv.) and an amine (or amino acid, see below), and slowly warmed to r.t. The reaction was monitored through LCMS and stirred until the complete conversion of the starting material MTMSK. It was quenched at 0° C. by dropwise addition of saturated solution of Na$_2$CO$_3$. It was concentrated under reduced pressure; the obtained aqueous phase was extracted with n-BuOH. The collected organic phase was concentrated followed by its purification by HPLC to obtain both the isomers of MTMSK-amine derivatives.

(S)-3'-MTMSK-Phe (23a):

Compound 23a (10.5 mg, 62%) was prepared following the general method of reductive amination mediated by NaBH$_3$CN taking MTMSK (15 mg, 0.014 mmol) and L-Phe-OMe.HCl (9 mg, 0.042 mmol) as substrates in presence of TEA (10 μL, 0.07 mmol) and acetic acid (200 μL) in methanol (2 mL) as a yellow flappy solid. $^1$H NMR (400 MHz, Methanol-d$_4$) δ 8.43 (d, J=2.0 Hz, 1H), 7.26-7.13 (m, 5H), 6.87 (s, 1H), 6.74 (s, 1H), 5.33 (d, J=9.6 Hz, 1H), 5.15

(d, J=9.4 Hz, 1H), 4.95 (s, 1H), 4.70 (d, J=9.6 Hz, 1H), 4.63 (d, J=10.9 Hz, 2H), 3.86-3.60 (m, 10H), 3.56 (d, J=2.0 Hz, 3H), 3.50 (s, 4H), 3.12-2.87 (m, 9H), 2.85-2.79 (m, 1H), 2.61-2.52 (m, 2H), 2.49-2.37 (m, 2H), 1.94-1.69 (m, 6H), 1.56 (q, J=10.9 Hz, 4H), 1.36-1.19 (m, 19H), 1.04 (d, J=6.4 Hz, 3H).

The stereochemistry of the newly generated stereocenter at C-3'-position was assigned following a 2D correlation experiment of compound. The stereochemistry at the C-3' position was determined by NOESY experiment. In fact, correlation of 3'-H ($\delta_H$=2.83 ppm) with 2'-H ($\delta_H$=3.72 ppm) indicates the β-orientation of —NHR. As the stereochemistry at 2' and 1' were predetermined and NOESY experiments reveals that 3'-H does not correlate with 2'-H, indicating α orientation of 3'-H.

TABLE

Initial cytotoxicity ($GI_{50}$) screen in TC32 (Ewing sarcoma) and PC3 (non-Ewing sarcoma) cell line of MTMSK analogues

| Entry | Analogues MTMSK Analogues | TC-32 Ewing sarcoma EWS-FLI1 Type 1 $GI_{50}$ (nM) | PC-3 Prostate cancer No ETS Translocation $GI_{50}$ (nM) | $GI_{50}$ ratio PC3:TC32 |
|---|---|---|---|---|
| 1 | 25a | 120 | 517 | 4.31 |
| 2 | 26a | 71 | 456 | 6.42 |
| 3 | MTM | 107 | 148 | 1.38 |

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Wohlert, S.; Künzel, E.; Machinek, R.; Mendez, C.; Salas, J.; Rohr, J. The structure of mithramycin reinvestigated. *J. Nat. Prod.* 1999, 62, 119-121.
2. Rohr, J.; Méndez, C.; Salas, J. A. The biosynthesis of aureolic acid group antibiotics. *Bioorg. Chem.* 1999, 27, 41-54.
3. Kofman, S.; Perlia, C. P, Economou, S. G. Mithramycin in the treatment of metastatic ewing's sarcoma. *Cancer* 1973, 31, 889-893; b) Balamuth, N., Womer, R. B.: Ewing's sarcoma, *Lancet Oncol.* 2010, 11, 184-192.
4. (a) Kofman, S.; Eisenstein, R. Mithramycin in the treatment of disseminated cancer. *Cancer Chemother. Rep.* 1963, 32, 77-96; (b) Kofman, S.; Medrek, T. J.; Alexander, R. W Mithramycin in the treatment of embryonal cancer. *Cancer* 1964, 17, 938-948.
5. Delattre, O.; Zucman, J.; Plougastel, B.; Desmaze, C.; Melot, T.; Peter, M.; Kovar, H.; Joubert, I.; de Jong, P.; Rouleau, G. Gene fusion with an ETS DNA-binding domain caused by chromosome translocation in human tumours. *Nature* 1992, 359, 162.
6. May, W. A.; Arvand, A.; Thompson, A. D.; Braun, B. S.; Wright, M.; Denny, C. T. EWS/FLI1-induced manic fringe renders NIH 3T3 cells tumorigenic. *Nat. Genet.* 1997, 17, 495-497.
7. Tomlins, S. A., Rhodes, D. R., Perner, S., Dhanasekaran, S. M., Mehra, R., Sun, X. W., Varambally, S., Cao, X., Tchinda, J., Kuefer, R. and Lee, C. Recurrent fusion of TMPRSS2 and ETS transcription factor genes in prostate cancer. *Science,* 2005, 310, 644-648.
8. Sastry, M.; Patel, D. J. Solution structure of the mithramycin dimer-DNA complex. *Biochemistry* 1993, 32, 6588-6604.
9. Remsing, L. L.; González, A. M.; Nur-e-Alam, M.; Fernández-Lozano, M. J.; Braña, A. F.; Rix, U.; Oliveira, M. A.; Méndez, C.; Salas, J. A.; Rohr, J. Mithramycin SK, a novel antitumor drug with improved therapeutic index, mithramycin SA, and demycarosyl-mithramycin SK: three new products generated in the mithramycin producer *Streptomyces argillaceus* through combinatorial biosynthesis. I *Am. Chem. Soc.* 2003, 125, 5745-5753.
10. Scott, D.; Chen, J. M.; Bae, Y.; Rohr, J. Semi-synthetic mithramycin SA derivatives with improved anti-cancer activity. *Chem. Biol. Drug. Des.* 2013, 81, 615-624.
11. Leggas, M.; Eckenrode, J.; Mitra, P.; Jha, J.; Salem, S.; Mandal, A.; Thorson, J.; Rohr, J. [abstract]. In: Proceedings of the AACR-NCI-EORTC international conference: molecular targets and cancer therapeutics; 2017 Oct. 26-30; philadelphia, PA. philadelphia (PA): AACR; *Mol Cancer Ther.* 2018, 17 (1 Suppl): Abstract nr B043.
12. Hou, C.; Weidenbach, S.; Cano, K. E.; Wang, Z.; Mitra, P.; Ivanov, D. N.; Rohr, J.; Tsodikov, O. V. Structures of mithramycin analogues bound to DNA and implications for targeting transcription factor FLI1. *Nucleic Acids Res.* 2016, 44, 8990-9004.
13. Alqahtani, N.; Porwal, S. K.; James, E. D.; Bis, D. M.; Karry, J. A.; Lane, A. L.; Viswanathan, R. Synergism between genome sequencing, tandem mass spectrometry and bio-inspired synthesis reveals insights into nocardioazine B biogenesis. *Org. Biomol. Chem.* 2015, 13, 7177-7192.
14. Cardoso, A. S. P.; Marques, M. M. B.; Srinivasan, N.; Prabhakar, S.; Lobo, A. M.; Rzepa, H. S. Studies in sigmatropic rearrangements of N-prenylindole derivatives—a formal enantiomerically pure synthesis of tryprostatin B. *Org. Biomol. Chem.* 2006, 4, 3966-3972.
15. Loach, R. P.; Fenton, O. S.; Amaike, K.; Siegel, D. S.; Ozkal, E.; Movassaghi, M. Derivatization of C3-alkylindoles including tryptophans and tryptamines. *J. Org. Chem.* 2014, 79, 11254-11263.
16. Partridge, B. M.; Hartwig, J. F. Sterically controlled iodination of arenes via iridium-catalyzed C—H borylation. *Org. Lett.* 2012, 15, 140-143.
17. Feng, Y.; Holte, D.; Zoller, J.; Umemiya, S.; Simke, L. R.; Baran, P. S. Total synthesis of erruculogen and fumitremorgin a enabled by ligand-controlled CH borylation. *J. Am. Chem. Soc.* 2015, 137, 10160-10163.
18. Jia, Y.; Zhu, J. Palladium-catalyzed, modular synthesis of highly functionalized indoles and tryptophans by direct annulation of substituted o-haloanilines and aldehydes. *J. Org. Chem.* 2006, 71, 7826-7834.
19. Kokotos, G.; Padron, J. M.; Martin, T.; Gibbons, W. A.; Martin, V. S. A general approach to the asymmetric synthesis of unsaturated lipidic α-amino acids. The first synthesis of α-aminoarachidonic acid. *J. Org. Chem.* 1998, 63, 3741-3744.
20. Bi, W; Bi, Y; Xue, P.; Zhang, Y; Gao, X.; Wang, Z.; Li, M.; Baudy-Floc'h, M.; Ngerebara, N.; Li, X. Novel β-carboline-tripeptide conjugates attenuate mesenteric ischemia/reperfusion injury in the rat. *Eur. J. Med. Chem.* 2011, 46, 2441-2452.
21. Coste, A.; Toumi, M.; Wright, K.; Razafimahaléo, V.; Couty, F.; Marrot, J.; Evano, G. Copper-catalyzed cyclization of iodo-tryptophans: A straightforward synthesis of pyrroloindoles. *Org. Lett.* 2008, 10, 3841-3844.
22. Cozett, R. E.; Venter, G. A.; Gokada, M. R.; Hunter, R. Catalytic enantioselective acyl transfer: the case for 23. Choi, J. Y.; Calvet, C. M.; Gunatilleke, S. S.; Ruiz, C.; Cameron, M. D.; McKerrow, J. H.; Podust, L. M.; Roush, W. R. Rational development of 4-aminopyridyl-based inhibitors targeting *Trypanosoma cruzi* CYP51 as antichagas agents. *J. Med. Chem.* 2013, 56, 7651-7668.

24. Osgood, C. L.; Maloney, N.; Kidd, C. G.; Kitchen-Goosen, S.; Segars, L.; Gebregiorgis, M.; Woldemichael, G. M.; He, M.; Sankar, S.; Lessnick, S. L.; Kang, M.; Smith, M.; Turner, L.; Madaj, Z. B.; Winn, M. E.; Núñez, L. E.; González-Sabín, Z.; Helman, L. J.; Morís, F.; Grohar, P. J. Identification of mithramycin analogues with improved targeting of the EWS-FLI1 transcription factor. *Clin. Cancer Res.* 2016, 22, 4105-4118.

25. Garcia-Aragoncillo, E., J. Carrillo, E. Lalli, N. Agra, G. Gomez-Lopez, A. Pestana, and J. Alonso. "DAX1, a direct target of EWS/FLI1 oncoprotein, is a principal regulator of cell-cycle progression in ewing's tumor cells." *Oncogene* 2008, 27, 6034-6043.

26. Grohar, P. J.; Woldemichael, G. M.; Griffin, L. B.; Mendoza, A.; Chen, Q.-R.; Yeung, C.; Currier, D. G.; Davis, S.; Khanna, C.; Khan, J. Identification of an inhibitor of the EWS-FLI1 oncogenic transcription factor by high-throughput screening. *J. Natl. Cancer Inst.* 2011, 103, 962-978.

27. U.S. Pat. No. 9,447,135 to Rohr, J. T, et al., "Semi-Synthetic Mithramycin Derivatives with Anti-Cancer Activity."

28. International Patent Application Publication No. WO 2010126626 to deLong, et al., "Preparation of isoquinolinylamide derivatives for use as dual-action monoamine transport and kinase inhibitors."

It will be understood that various details of the presently disclosed subject matter can be changed without departing from the scope of the subject matter disclosed herein. Furthermore, the foregoing description is for the purpose of illustration only, and not for the purpose of limitation.

```
SEQUENCE LISTING
SEQ ID NO: 01:
   1 pgsggiglwg fllellsdsa nascitwegt ngefkmtdpd evarrwgerk
     skpnmnydkl sralryyydk nimtkvhgkr yaykfdfhgi aqalqphp 98

SEQ ID NO: 02
   1 pgsgqiqlwq fllellsdss nsscitwegt ngefkmtdpd evarrwgerk
     skpnmnydkl sralryyydk nimtkvhgkr yaykgdghgi aqalqphp 98

SEQ ID NO: 03 - amino acid sequence of FLI1 transcription
factor, with the DNA binding domain in that sequence highlighted.
   1 mdgtikeals vvsddgslfd saygaaahlp kadmtasgsp dygqphkinp lppqqewinq 61 pvrvnvkrey dhmngsresp vdcsvskcsk lvgggesnpm nynsymdekn gppppnmttn 121 errvivpadp tlwtqehvrq wlewaikeys lmeidtsffq nmdgkelckm nkedflratt 181 lyntevllsh lsylressll aynttshtdq ssrlsvkedp sydsvrrgaw gnnmnsglnk 241 spplggagti sknteqrpqp dpyqilgpts srlanpgsgq iqlwgfllel lsdsanasci 301 twegtngefk mtdpdevarr wgerkskpnm nydklsralr yyydknimtk vhgkryaykf 361 dfhgiagalg phptessmyk ypsdisymps yhahqqkvnf vpphpssmpv tsssffgaas 421 gywtsptggi ypnpnvprhp nthvpshlgs yy SEQ ID NO: 04 - amino acid sequence of ERG transcription factor,
with the DNA binding domain in that sequence highlighted.
   1 miqtvpdpaa hikealsvvs edgslfecay gtphlaktem tassssdygq tskmsprvpq 61 gdwlsqppar vtikmecnps gvngsrnspd ecsvakggkm vgspdtvgmn ygsymeekhm 121 pppnmttner rvivpadptl wstdhvrgwl ewavkeyglp dvnillfqni dgkelckmck 181 ddfgrltpsy nadillshlh ylretplphl tsddvdkalq nsprlmharn tdlpyepprr 241 sawtghghpt pqskaaqpsp stvpktedqr pqldpyqilg ptssrlanpg sgqiqlwqfl 301 lellsdssns scitwegtng efkmtdpdev arrwgerksk pnmnydklsr alryyydkni 361 mtkvhgkrya ykfdfhgiaq algphppess lykypsdlpy mgsyhahpqk mnfvaphppa 421 lpvtsssffa apnpywnspt ggiypntrlp tshmpshlgt yy
```

The invention claimed is:

1. A mithramycin (MTM) short side chain ketone (SK) derivatives and MTM short side chain diketone (SDK) derivative having the following formula:

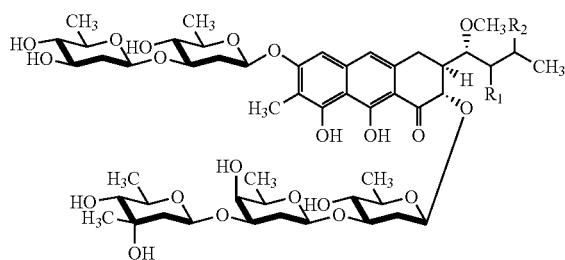

or a pharmaceutically acceptable salt thereof, wherein $R^1$ is =O or —OH, and $R^2$ is (a) a substituted tryptophan (Trp) or phenylalanine (Phe) derivative having a substitution on a phenyl or indole ring of the Trp or Phe derivative, wherein the substitution is selected from the group consisting of lower alkyl, prenyl, aryl, alkylaryl, alkoxyl, nitro, halogen, and halocarbon;

(b) a substituted Trp, Phe, Trp-Phe, or Phe-Trp dipeptide derivative having a substitution on a phenyl or indole ring of the dipeptide derivative, wherein the substitution is selected from the group consisting of lower alkyl, prenyl, aryl, alkylaryl, alkoxyl, nitro, halogen, and halocarbon; or (c) an unsubstituted Trp, Phe, Trp-Phe, or Phe-Trp dipeptide derivative.

2. The MTM SK or MTM SDK derivative of claim 1, wherein $R^2$ is a substituted tryptophan (Trp) derivative.

3. The MTM SK or MTM SDK derivative of claim 1, having the following formula:

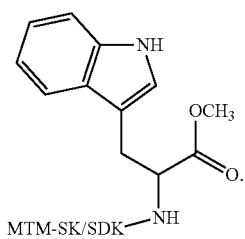

4. The MTM SK or MTM SDK derivative of claim 1, having the following formula:

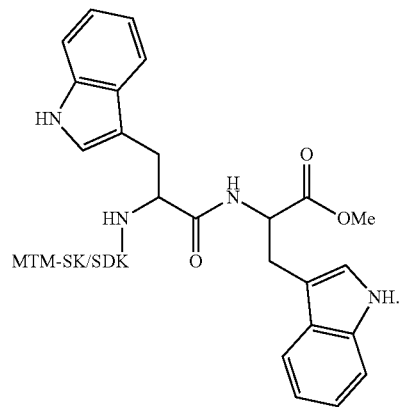

5. The MTM SK or MTM SDK derivative of claim 1, wherein $R^2$ is a substituted phenylalanine (Phe) derivative.

6. The MTM SK or MTM SDK derivative of claim 1, having the following formula:

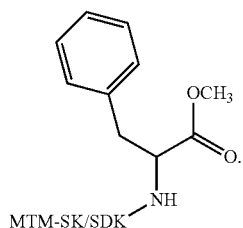

7. The MTM SK or MTM SDK derivative of claim 1, wherein $R^2$ is Trp, Phe, Trp-Phe, or Phe-Trp dipeptide derivative.

8. The MTM SK or MTM SDK derivative of claim 1, selected from the formulae consisting of:

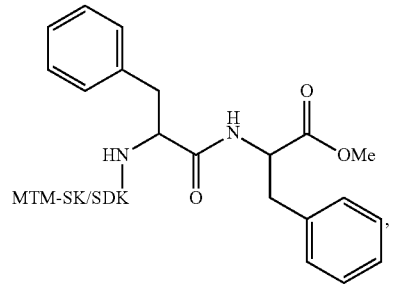

-continued

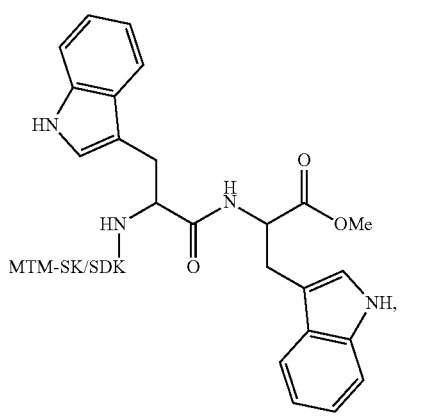

and

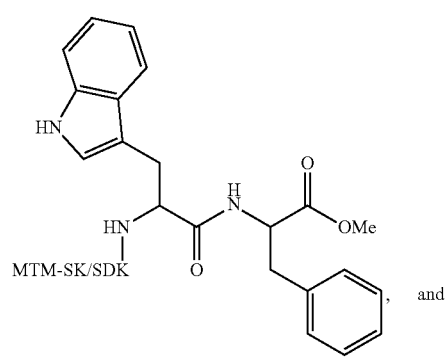

, and

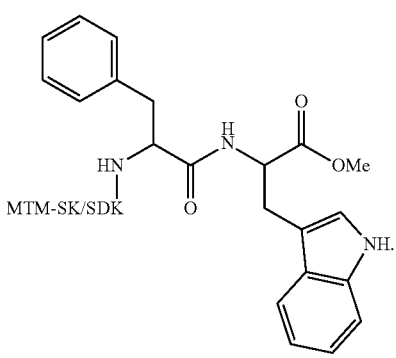

9. The MTM SK or MTM SDK derivative of claim 1, wherein the substituted amino acid dipeptide derivative is a substituted Trp, Phe, Trp-Phe, or Phe-Trp dipeptide derivative.

10. The MTM SK or MTM SDK derivative of claim 1, wherein the unsubstituted dipeptide derivative is an unsubstituted Trp, Phe, Trp-Phe, or Phe-Trp dipeptide derivative.

11. The MTM SK or MTM SDK derivative of claim 1, having the following formula:

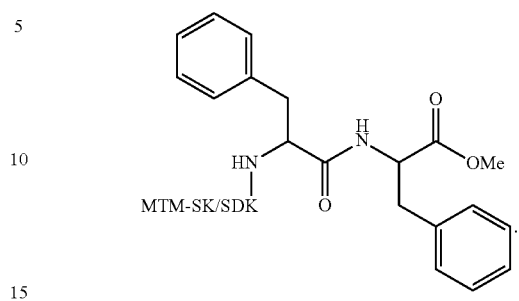

12. The MTM SK or MTM SDK derivative of claim 1, having the following formula:

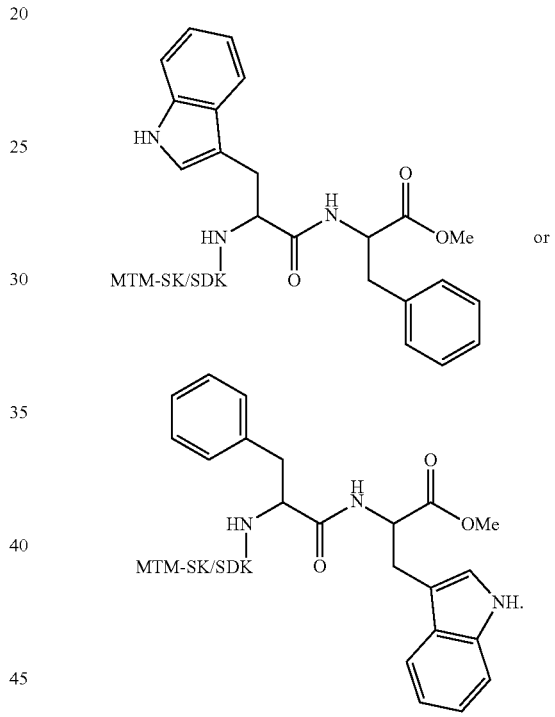

13. A method of treating cancer or neuro-disease in a patient in need thereof, the method comprising administering to the patient a therapeutically effective amount of the MTM SK or MTM SDK derivative or a pharmaceutically acceptable salt thereof of claim 1.

14. The method of claim 13, for the treatment of Ewing sarcoma.

15. The method of claim 13, for the treatment of lung cancer.

16. The method of claim 13, for the treatment of leukemia or lymphoma.

17. The method of claim 13, for the treatment of colon cancer.

18. A method for selectively modulating the activity of a target ETS transcription factor in a patient in need thereof, including administering to the patient a therapeutically effective amount of an MTM SK or MTM SDK derivative or a pharmaceutically acceptable salt thereof of claim 1.

* * * * *

SEQUENCE LISTING

<160> NUMBER OF SEQ ID NOS: 4

<210> SEQ ID NO 1
<211> LENGTH: 98
<212> TYPE: PRT

```
<213> ORGANISM: Artificial Sequence
<220> FEATURE:
<223> OTHER INFORMATION: recombinant

<400> SEQUENCE: 1

Pro Gly Ser Gly Gln Ile Gln Leu Trp Gln Phe Leu Leu Glu Leu Leu
1               5                   10                  15

Ser Asp Ser Ala Asn Ala Ser Cys Ile Thr Trp Glu Gly Thr Asn Gly
            20                  25                  30

Glu Phe Lys Met Thr Asp Pro Asp Glu Val Ala Arg Arg Trp Gly Glu
        35                  40                  45

Arg Lys Ser Lys Pro Asn Met Asn Tyr Asp Lys Leu Ser Arg Ala Leu
    50                  55                  60

Arg Tyr Tyr Tyr Asp Lys Asn Ile Met Thr Lys Val His Gly Lys Arg
65                  70                  75                  80

Tyr Ala Tyr Lys Phe Asp Phe His Gly Ile Ala Gln Ala Leu Gln Pro
                85                  90                  95

His Pro

<210> SEQ ID NO 2
<211> LENGTH: 98
<212> TYPE: PRT
<213> ORGANISM: Artificial Sequence
<220> FEATURE:
<223> OTHER INFORMATION: recombinant

<400> SEQUENCE: 2

Pro Gly Ser Gly Gln Ile Gln Leu Trp Gln Phe Leu Leu Glu Leu Leu
1               5                   10                  15

Ser Asp Ser Ser Asn Ser Ser Cys Ile Thr Trp Glu Gly Thr Asn Gly
            20                  25                  30

Glu Phe Lys Met Thr Asp Pro Asp Glu Val Ala Arg Arg Trp Gly Glu
        35                  40                  45

Arg Lys Ser Lys Pro Asn Met Asn Tyr Asp Lys Leu Ser Arg Ala Leu
    50                  55                  60

Arg Tyr Tyr Tyr Asp Lys Asn Ile Met Thr Lys Val His Gly Lys Arg
65                  70                  75                  80

Tyr Ala Tyr Lys Phe Asp Phe His Gly Ile Ala Gln Ala Leu Gln Pro
                85                  90                  95

His Pro

<210> SEQ ID NO 3
<211> LENGTH: 452
<212> TYPE: PRT
<213> ORGANISM: Artificial Sequence
<220> FEATURE:
<223> OTHER INFORMATION: recombinant

<400> SEQUENCE: 3

Met Asp Gly Thr Ile Lys Glu Ala Leu Ser Val Val Ser Asp Asp Gln
1               5                   10                  15

Ser Leu Phe Asp Ser Ala Tyr Gly Ala Ala Ala His Leu Pro Lys Ala
            20                  25                  30

Asp Met Thr Ala Ser Gly Ser Pro Asp Tyr Gly Gln Pro His Lys Ile
        35                  40                  45

Asn Pro Leu Pro Pro Gln Gln Glu Trp Ile Asn Gln Pro Val Arg Val
    50                  55                  60

Asn Val Lys Arg Glu Tyr Asp His Met Asn Gly Ser Arg Glu Ser Pro
```

```
            65                  70                  75                  80
Val Asp Cys Ser Val Ser Lys Cys Ser Lys Leu Val Gly Gly Gly Glu
                    85                  90                  95

Ser Asn Pro Met Asn Tyr Asn Ser Tyr Met Asp Glu Lys Asn Gly Pro
                100                 105                 110

Pro Pro Pro Asn Met Thr Thr Asn Glu Arg Arg Val Ile Val Pro Ala
                115                 120                 125

Asp Pro Thr Leu Trp Thr Gln Glu His Val Arg Gln Trp Leu Glu Trp
            130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
                180                 185                 190

Tyr Leu Arg Glu Ser Ser Leu Leu Ala Tyr Asn Thr Thr Ser His Thr
            195                 200                 205

Asp Gln Ser Ser Arg Leu Ser Val Lys Glu Asp Pro Ser Tyr Asp Ser
        210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
            275                 280                 285

Glu Leu Leu Ser Asp Ser Ala Asn Ala Ser Cys Ile Thr Trp Glu Gly
        290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
                325                 330                 335

Arg Ala Leu Arg Tyr Tyr Asp Lys Asn Ile Met Thr Lys Val His
                340                 345                 350

Gly Lys Arg Tyr Ala Tyr Lys Phe Asp Phe His Gly Ile Ala Gln Ala
            355                 360                 365

Leu Gln Pro His Pro Thr Glu Ser Ser Met Tyr Lys Tyr Pro Ser Asp
370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
            420                 425                 430

Asn Pro Asn Val Pro Arg His Pro Asn Thr His Val Pro Ser His Leu
                435                 440                 445

Gly Ser Tyr Tyr
        450

<210> SEQ ID NO 4
<211> LENGTH: 460
<212> TYPE: PRT
<213> ORGANISM: Artificial Sequence
```

```
<220> FEATURE:
<223> OTHER INFORMATION: recombinant

<400> SEQUENCE: 4

Met Ile Gln Thr Val Pro Asp Pro Ala Ala His Ile Lys Glu Ala Leu
1               5                   10                  15

Ser Val Val Ser Asp Glu Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
210                 215                 220

Leu Met His Ala Arg Asn Thr Asp Leu Pro Tyr Glu Pro Pro Arg Arg
225                 230                 235                 240

Ser Ala Trp Thr Gly His Gly His Pro Thr Pro Gln Ser Lys Ala Ala
                245                 250                 255

Gln Pro Ser Pro Ser Thr Val Pro Lys Thr Glu Asp Gln Arg Pro Gln
            260                 265                 270

Leu Asp Pro Tyr Gln Ile Leu Gly Pro Thr Ser Ser Arg Leu Ala Asn
        275                 280                 285

Pro Gly Ser Gly Gln Ile Gln Leu Trp Gln Phe Leu Leu Glu Leu Leu
    290                 295                 300

Ser Asp Ser Ser Asn Ser Ser Cys Ile Thr Trp Glu Gly Thr Asn Gly
305                 310                 315                 320

Glu Phe Lys Met Thr Asp Pro Asp Glu Val Ala Arg Arg Trp Gly Glu
                325                 330                 335

Arg Lys Ser Lys Pro Asn Met Tyr Asp Lys Leu Ser Arg Ala Leu Arg
            340                 345                 350

Tyr Tyr Tyr Asp Lys Asn Ile Met Thr Lys Val His Gly Lys Arg Tyr
        355                 360                 365

Ala Tyr Lys Phe Asp Phe His Gly Ile Ala Gln Ala Leu Gly Pro His
    370                 375                 380

Gln Gln Glu Ser Ser Leu Tyr Lys Tyr Pro Ser Asp Leu Pro Tyr Met
385                 390                 395                 400
```

```
Gly Ser Tyr His Ala His Pro Gln Lys Met Asn Phe Val Ala Pro His
            405             410                 415
Pro Pro Ala Leu Pro Val Thr Ser Ser Ser Phe Ala Ala Pro Asn
            420             425             430
Pro Tyr Trp Asn Ser Pro Thr Gly Gly Tyr Pro Asn Thr Arg Leu Pro
            435             440                 445
Thr Ser His Met Pro Ser His Leu Gly Thr Tyr Tyr
450                 455             460
```